United States Patent
Zdeblick

(10) Patent No.: US 8,204,586 B2
(45) Date of Patent: Jun. 19, 2012

(54) EXTERNAL CONTINUOUS FIELD TOMOGRAPHY

(75) Inventor: Mark Zdeblick, Portola Valley, CA (US)

(73) Assignee: Proteus Biomedical, Inc., Redwood City, CA (US)

(*) Notice: Subject to any disclaimer, the term of this patent is extended or adjusted under 35 U.S.C. 154(b) by 601 days.

(21) Appl. No.: 11/562,690

(22) Filed: Nov. 22, 2006

(65) Prior Publication Data

US 2007/0135721 A1 Jun. 14, 2007

Related U.S. Application Data

(60) Provisional application No. 60/739,804, filed on Nov. 22, 2005.

(51) Int. Cl.
*A61B 5/04* (2006.01)
(52) U.S. Cl. ........ 600/547; 600/508; 600/509; 600/513; 600/515; 600/393; 607/4; 607/5; 607/6; 607/32; 607/36
(58) Field of Classification Search .......... 607/4–6, 607/9, 17, 18, 122, 2, 32, 36, 40, 48, 60; 600/547, 374, 508–509, 513, 515, 382, 393, 600/347
See application file for complete search history.

(56) References Cited

U.S. PATENT DOCUMENTS

| | | |
|---|---|---|
| 4,140,131 A | 2/1979 | Dutcher et al. |
| 5,154,183 A | 10/1992 | Kreyehagen et al. |
| 5,515,848 A | 5/1996 | Corbett, III et al. |
| 5,571,148 A | 11/1996 | Loeb et al. |
| 5,662,108 A * | 9/1997 | Budd et al. ............ 600/374 |
| 5,772,108 A | 6/1998 | Ruggiere, Sr. et al. |
| 5,963,429 A | 10/1999 | Chen |
| 5,983,126 A | 11/1999 | Wittkampf |
| 5,999,848 A | 12/1999 | Gord et al. |
| 6,038,480 A | 3/2000 | Hrdlicka et al. |
| 6,208,894 B1 | 3/2001 | Schulman et al. |
| 6,259,937 B1 | 7/2001 | Schulman et al. |
| 6,266,567 B1 | 7/2001 | Ishikawa et al. |
| 6,366,815 B1 | 4/2002 | Haugland et al. |
| 6,366,819 B1 | 4/2002 | Stokes |

(Continued)

FOREIGN PATENT DOCUMENTS

EP 1356847 10/2003

(Continued)

OTHER PUBLICATIONS

Neurostimulation Device Trends, Boston Scientific; Sep. 2, 2009, 1 pp.

*Primary Examiner* — Niketa Patel
*Assistant Examiner* — Rex R Holmes
(74) *Attorney, Agent, or Firm* — Bozicevic, Field & Francis LLP; Bret E. Field

(57) ABSTRACT

Methods for evaluating tissue motion of a tissue location, e.g., a cardiac location, via external continuous field tomography are provided. Aspects of the methods include generating at least one substantially linear continuous field gradient across the tissue location of interest, and using a resultant signal from a sensing element stably associated with the tissue location to evaluate motion of the tissue location. Also provided are systems, devices and related compositions for practicing the subject methods. The subject methods and devices find use in a variety of different applications, including cardiac resynchronization therapy.

25 Claims, 5 Drawing Sheets

U.S. PATENT DOCUMENTS

| | | |
|---|---|---|
| 6,584,362 B1 | 6/2003 | Scheiner et al. |
| 6,662,055 B1 | 12/2003 | Prutchi |
| 6,895,283 B2 | 5/2005 | Erickson et al. |
| 7,096,070 B1 | 8/2006 | Jenkins et al. |
| 2002/0045810 A1* | 4/2002 | Ben-Haim .................. 600/374 |
| 2003/0065365 A1 | 4/2003 | Zhu et al. |
| 2003/0088303 A1 | 5/2003 | Goode |
| 2003/0216630 A1 | 11/2003 | Jersey-Willuhn et al. |
| 2003/0233134 A1 | 12/2003 | Greenberg et al. |
| 2004/0193021 A1 | 9/2004 | Zdeblick et al. |
| 2005/0038481 A1 | 2/2005 | Chinchoy et al. |
| 2005/0090870 A1 | 4/2005 | Hine et al. |
| 2005/0096647 A1 | 5/2005 | Steinke et al. |
| 2005/0148832 A1 | 7/2005 | Reghabi et al. |
| 2006/0058588 A1 | 3/2006 | Zdeblick |
| 2006/0241711 A1 | 10/2006 | Sathaye |
| 2007/0135721 A1 | 6/2007 | Zdeblick et al. |
| 2007/0161914 A1 | 7/2007 | Zdeblick et al. |
| 2007/0173896 A1 | 7/2007 | Zdeblick et al. |
| 2007/0173897 A1 | 7/2007 | Zdeblick et al. |
| 2007/0185549 A1 | 8/2007 | Zdeblick et al. |
| 2008/0077186 A1 | 3/2008 | Thompson et al. |
| 2009/0062881 A1 | 3/2009 | Gross et al. |

FOREIGN PATENT DOCUMENTS

| | | |
|---|---|---|
| WO | 2006029090 | 3/2006 |
| WO | WO2006042039 A2 | 4/2006 |
| WO | 2006069323 | 6/2006 |
| WO | WO2006069322 A2 | 6/2006 |

* cited by examiner

EXTERNAL CONTINUOUS FIELD TOMOGRAPHY

CROSS-REFERENCE TO RELATED APPLICATIONS

This application claims priority to: U.S. Provisional Application Ser. No. 60/739,804 filed on Nov. 22, 2005; the disclosure of which priority application is herein incorporated by reference.

INTRODUCTION

Background

In a diverse array of applications, the evaluation of tissue motion is desirable, e.g., for diagnostic or therapeutic purposes. An example of where evaluation of tissue motion is desirable is cardiac resynchronization therapy (CRT), where evaluation of cardiac tissue motion is employed for diagnostic and therapeutic purposes.

CRT is an important new medical intervention for patients suffering from heart failure, e.g., congestive heart failure (CHF). When congestive heart failure occurs, symptoms develop due to the heart's inability to function sufficiently. Congestive heart failure is characterized by gradual decline in cardiac function punctuated by severe exacerbations leading eventually to death. It is estimated that over five million patients in the United States suffer from this malady.

The aim of resynchronization pacing is to induce the interventricular septum and the left ventricular free wall to contract at approximately the same time.

Resynchronization therapy seeks to provide a contraction time sequence that will most effectively produce maximal cardiac output with minimal total energy expenditure by the heart. The optimal timing is calculated by reference to hemodynamic parameters such as dP/dt, the first time-derivative of the pressure waveform in the left ventricle. The dP/dt parameter is a well-documented proxy for left ventricular contractility.

In current practice, external ultrasound measurements are used to calculate dP/dt. Such external ultrasound is used to observe wall motion directly. Most commonly, the ultrasound operator uses the ultrasound system in a tissue Doppler mode, a feature known as tissue Doppler imaging (TDI), to evaluate the time course of displacement of the septum relative to the left ventricle free wall. The current view of clinicians is that ultrasonographic evaluation using TDI or a similar approach may become an important part of qualifying patients for CRT therapy.

A useful diagnostic imaging approach in current practice is to provide planar section views of the organ of interest, such as the heart. These views are very familiar to clinicians, and provide excellent therapeutically relevant medical information.

As currently delivered, CRT therapy is effective in about half to two-thirds of patients implanted with a resynchronization device. In approximately one-third of these patients, this therapy provides a two-class improvement in patient symptoms as measured by the New York Heart Association scale. In about one-third of these patients, a one-class improvement in cardiovascular symptoms is accomplished. In the remaining third of patients, there is no improvement or, in a small minority, a deterioration in cardiac performance. This group of patients is referred to as non-responders. It is possible that the one-class New York Heart Association responders are actually marginal or partial responders to the therapy, given the dramatic results seen in a minority.

The synchronization therapy, in order to be optimal, targets the cardiac wall segment point of maximal delay, and advances the timing to synchronize contraction with an earlier contracting region of the heart, typically the septum. However, the current placement technique for CRT devices is usually empiric. A physician will cannulate a vein that appears to be in the region described by the literature as most effective. The device is then positioned, stimulation is carried out, and the lack of extra-cardiac stimulation, such as diaphragmatic pacing, is confirmed. With the currently available techniques, rarely is there time or means for optimizing cardiac performance.

When attempted today, CRT optimization must be preformed by laborious manual method of an ultrasonographer evaluating cardiac wall motion at different lead positions and different interventricular delay (IVD) settings. The IVD is the ability of pacemakers to be set up with different timing on the pacing pulse that goes to the right ventricle versus the left ventricle. In addition, all pacemakers have the ability to vary the atrio-ventricular delay, which is the delay between stimulation of the atria and the ventricle or ventricles themselves. These settings can be important in addition to the location of the left ventricular stimulating electrode itself in resynchronizing the patient.

More generally, CHF patients today are primarily managed on the basis of self-reported symptoms. In many cases, a patient's cardiovascular performance gradually deteriorates, with only mild subjective symptoms, until emergency admission to the hospital is required. The physician's ability to intervene early in the decompensation process—when cardiac performance is objectively declining but symptoms are not yet severe—is hampered by the lack of objective cardiac performance data characterizing the patient's condition.

A related issue is the primarily symptomatic management of patients with or without heart failure in the setting of progressive ischemic heart disease. Interventional cardiologists today have no reliable way of detecting an acute onset or worsening of cardiac ischemia when it is at an early, asymptomatic stage. If detected at this early stage, the ischemia is potentially reversible via a timely intervention. However, progressive akinesis, caused by stiffening of the cardiac muscle, is a hallmark of ischemia and is observable well before changes in the electrocardiogram (ECG) or in circulating cardiac enzymes.

Another issue is that cardiac rhythm management (CRM) systems rely upon computerized analyses of intracardiac electrograms to determine whether a pathologic arrhythmia exists and, following therapy, to characterize patients' response. Electrophysiologic-only arrhythmia detection algorithms can sometimes be confused by electrical noise and other non-cardiac interference.

It would be desirable to include objective data describing the motion of the heart to improve the reliability of such algorithms. It would be particularly useful if the data could be provided non-invasively in a doctor's office with external sensors which produce information similar to that available in a cross-sectional view, but which avoid the high radiation levels required with fluoroscopy imaging.

Relevant Literature

Publications of interest include: U.S. Pat. Nos. 5,772,108; 5,983,126 and U.S. Published Patent Application No. 2005/0038481.

SUMMARY

Methods for evaluating tissue motion, such as the motion of a cardiac location, e.g., heart wall, via continuous field tomography using broadcasting elements placed externally about the body are provided. Embodiments of the methods include generating one or more substantially linear continuous, e.g., electric, field gradients across a region of the subject that includes a target tissue location of interest. Resultant readings at one or more continuous field sensing elements, e.g., electrodes, stably associated with a target tissue location of interest are then obtained to evaluate movement of the target tissue location. This data generated by the present innovative method provides a view of the organ analogous to classic radiological segmental profiles. Also provided are systems, devices and related compositions for practicing the subject methods. The subject methods and devices find use in a variety of different applications, including cardiac resynchronization therapy.

DETAILED DESCRIPTION

Figure 1:
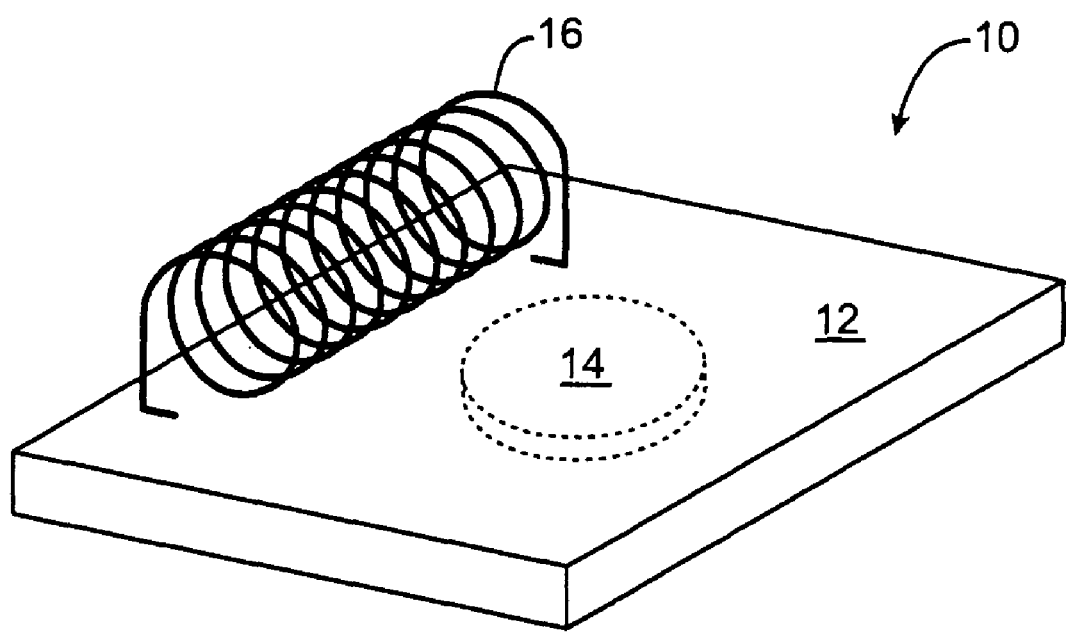
FIG. 1 provides a view of a skin contacting electrode with a broadcast coil.

In the present invention, continuous field tomographic methods for evaluating motion of a tissue location(s), such as the motion of a cardiac location, e.g., heart wall, are provided. Embodiments of the methods include generating one or more substantially linear or "flat" continuous fields across a portion of the body which includes the target tissue location(s). Gradient dependent readings are then obtained from sensing elements stably associated with the target tissue location and the readings are employed to evaluated motion of the target location. Also provided are systems, devices and related compositions for practicing the subject methods. The subject methods and devices find use in a variety of different applications, including cardiac resynchronization therapy.

In further describing various aspects of the subject invention, certain embodiments of the methods are first reviewed both in general terms and in the context of embodiments of devices and systems that may be employed to practice the methods. Following this section, representative applications in which the subject invention finds use are described, as well as other aspects of the invention, such as computer related embodiments and kits.

Methods

As summarized above, the subject invention provides continuous field tomography methods for evaluating movement of a tissue location of interest. In the subject tomography methods, data obtained by a sensing element stably associated with the tissue location of interest as it moves through an applied continuous field are employed. While the methods may be viewed as tomography methods, such a characterization does not mean that the methods are necessarily employed to obtain a map of a given tissue location, such as a 2-dimensional or 3-dimensional map. The characterization refers instead to the fact that that changes in a sensing element as it moves through an applied continuous field are used to evaluate or characterize a tissue location in some way.

By "continuous field tomography method" is meant a method which employs detected changes in an applied continuous field to obtain a signal, which signal is then employed to determine tissue location movement. For the purposes of this application, the term "continuous field" means a field from which tomography measurement data is obtained from the field's continuous aspect. The continuous field is one or more cycles of a sine wave. There is no necessary requirement for discontinuity in the field to obtain data. As such, the applied field employed in the subject invention is continuous over a given period of time.

The "continuous field" used for tomography measurement may, at times, be provided with disruptions or naturally have some disruptions, and still fall within the present meaning of "continuous field". As clarifying examples, pulsing the field to conserve power or mutiplexing between different fields remains within the meaning of "continuous field" for the purposes of the present invention.

As summarized above, the subject invention provides methods of evaluating movement of a tissue location. "Evaluating" is used herein to refer to any type of detecting, assessing or analyzing, and may be qualitative or quantitative. In representative embodiments, movement can be determined relative to another tissue location, such that the methods are employed to determine movement of two or more tissue locations relative to each other.

The tissue location(s) may be a defined location or portion of a body, i.e., subject, where in certain embodiments it is a defined location or portion (i.e., domain or region) of a body structure, such as an organ, where in representative embodiments the body structure is an internal body structure (i.e., an internal tissue location), such as an internal organ, e.g., heart, kidney, stomach, lung, etc. In certain embodiments, the tissue location is a cardiac location. As such and for ease of further description, the various aspects of the invention are now reviewed in terms of evaluating motion of a cardiac location. The cardiac location may be either endocardial or epicardial, as desired, and may be an atrial or ventricular location. Where the tissue location is a cardiac location, in certain embodiments, the cardiac location is a heart wall location, e.g., a chamber wall, such as a ventricular wall, a septal wall, etc. Although the invention is now further described in terms of cardiac motion evaluation embodiments, the invention is not so limited, the invention being readily adaptable to evaluation of movement of a wide variety of different tissue locations.

In practicing embodiments of the invention, following implantation of any required elements in a subject (e.g., using surgical techniques), the first step is to set up or produce, i.e., generate, a substantially linear field gradient in a manner such that the tissue location(s) of interest is present in the generated continuous field. In certain embodiments, a single continuous substantially linear field gradient field is generated, while in other embodiments a plurality of different continuous fields are generated, e.g., two or more, such as three or more, four or more, five or more, 10 or more, 20 or more, etc.

In practicing embodiments of the subject methods, the applied continuous field(s) may be applied using any convenient format, so long as the tissue location(s) of interest resides in the applied continuous field. As such, in certain embodiments the applied continuous field is applied from an external body location, e.g., from a body surface location. For the purposes of this application, "external" means outside the core body, by example subcutaneously, topical, etc.

In the subject methods, following generation of the applied continuous field, as described above, a signal (representing data) from a continuous field sensing element that is stably associated with the tissue location of interest is then detected to evaluate movement of the tissue location. In certain embodiments, a signal from the sensing element is detected at least twice over a duration of time, e.g., to determine whether a parameter(s) being sensed by the sensing element has changed or not over the period of time, and therefore whether or not the tissue location of interest has moved over the period of time of interest. In certain embodiments, a change in a parameter is detected by the sensing element to evaluate movement of the tissue location.

In certain embodiments, at least one parameter of the applied continuous field is detected by the sensing element at two or more different times. Parameters of interest include, but are not limited to; amplitude, phase and frequency of the applied continuous field, as reviewed in greater detail below. In certain embodiments, the parameter of interest is detected at the two or more different times in a manner such that one or more of the other of the three parameters is substantially constant, if not constant.

By "stably associated with" is meant that the sensing element is substantially if not completely fixed relative to the tissue location of interest such that when the tissue location of interest moves, the sensing element also moves. As the employed continuous field sensing element is stably associated with the tissue location, its movement is at least a proxy for, and in certain embodiments is the same as, the movement of the tissue location to which it is stably associated, such that movement of the sensing element can be used to evaluate movement of the tissue location of interest. The continuous field sensing element may be stably associated with the tissue location using any convenient approach, such as by attaching the sensing element to the tissue location by using an attachment element, such as a hook, etc., by having the sensing element on a structure that compresses the sensing element against the tissue location such that the two are stably associated, etc.

In a given embodiment, the sensing element can provide output in an interval fashion or continuous fashion for a given duration of time, as desired.

In certain embodiments, a single sensing element is employed. In such methods, evaluation may include monitoring movement of the tissue location over a given period of time. In certain embodiments, two or more distinct sensing elements are employed to evaluate movement of two or more distinct tissue locations. The number of different sensing elements that are employed in a given embodiment may vary greatly, where in certain embodiments the number employed is 2 or more, such as 3 or more, 4 or more, 5 or more, 8 or more, 10 or more, etc. In such multi-sensor embodiments, the methods may include evaluating movement of the two or more distinct locations relative to each other.

In certain embodiments, the subject methods include providing a system that includes: (a) an external substantially linear continuous field generation element; and (b) a continuous field sensing element that is stably associated with the tissue location of interest. This providing step may include either implanting one or more new elements into a body, or simply employing an already existing implanted system, e.g., a pacing system, e.g., by using an adapter (for example a module that, when operationally connected to a pre-existing implant, enables the implant to perform the subject methods. This step, if employed, may be carried out using any convenient protocol, where a variety of protocols are well known to those of skill in the art.

The subject methods may be used in a variety of different kinds of animals, where the animals are typically "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In many embodiments, the subjects or patients will be humans.

The tissue movement evaluation data obtained using the subject methods may be employed in a variety of different applications, including but not limited to monitoring applications, treatment applications, etc. Certain applications in which the data obtained from the subject methods finds use are further reviewed in greater detail below.

With respect to the subject methods, the nature of the applied continuous field employed in the subject methods may vary depending on the particular application. The inventive continuous field tomography devices and methods enjoy a rich diversity of technical approaches. By example, an extraordinarily broad range of continuous field sources can be utilized in the inventive devices to make tomography measurement of the structure and movement of internal anatomical features. Electric, magnetic, acoustic, pressure waves, light and even heat can be utilized to provide this uniquely informative clinical information.

In certain embodiments, the continuous field that is applied is a wave field. In certain embodiments, the wave field is an electromagnetic wave. Representative electromagnetic continuous fields of interest include, but are not limited to: electrical and magnetic fields, as well as light. In yet other representative embodiments, the wave is a pressure wave, where a representative continuous field of this type is an acoustic field.

From changes determined in these measurements obtained from the continuous field sensing element, the dynamics and timing of tissue movement can be derived. This rich source of data allows the generation of both physical anatomical dimensions and the physiological functions which they bespeak, typically in real time.

While a number of different types of continuous field may be employed, in certain embodiments the continuous field is an electric field, e.g., an AC field. In these embodiments, the methods includes generating one or more substantially linear gradient or flat electric fields across a region or portion of the subject that includes the sensing element, and then obtaining linear field gradient dependent readings (e.g. in the form of an AC voltage) from the sensing element (e.g., a receive electrode) to evaluate motion of the target tissue location. As reviewed in greater detail below, external electrodes are employed as broadcasting electrodes to generate the one or more substantially linear electric field gradients. These external broadcasting electrodes may be positioned circumferentially around the region of interest. A change in the electric field broadcast by external or skin associated electrodes is sensed by receive electrode, and a resultant signal from the receive electrode is employed to evaluate movement of the tissue location.

Continuous External Electrical Field Tomography

One embodiment of the subject invention is continuous external electrical field tomography. An underlying focus of certain embodiments of the present invention is to measure the precise location of electrodes located internally at a target tissue location, e.g., inside the heart or elsewhere in the body. This goal is accomplished by obtaining a linear field gradient dependent reading from a sensing element stably associated with a tissue location(s) by measuring the signals, e.g., voltages (such as AC voltages), of those internal electrodes relative to a set of two or more pairs of external broadcasting electrodes, e.g., arrays of electrodes placed on the skin of the body or underneath the skin of the body.

The substantially linear or "flat" electric field gradients may be generated using any convenient protocol. In certain embodiments, sets of two or more pairs of external broadcasting electrodes are employed to generate the electric field gradients across the region of the body. A given set may be made up of two or more pairs, e.g., three or more pairs, five or more pairs, 10 or more pairs, 20 or more pairs, etc. As developed in greater detail below, the external electrodes may be arranged in a variety of different formats, e.g., approximately circumferentially about the body. In generating the electric field from the external electrodes, multiple frequencies may be created simultaneously, where there is a linear gradient in a given AC field at a given frequency across the body.

The electrodes which are in the circumference of the body create a relatively flat field, i.e., a substantially linear electric field gradient. This approach produces a substantially uniform gradient through the body at each frequency. Multiple frequencies are broadcast simultaneously using the multiple external broadcasting electrodes.

An idealized configuration of a broadcast electrode that may be employed in embodiments of the present invention is shown in FIG. 1. In FIG. 1, the electrode 10 is provided with a solid support 12 which includes processing capability, e.g., an integrated circuit silicon chip or a PC board, among other possibilities. At one surface, an electrode element 14, e.g., a silver chloride electrode, is provided that is used to contact the skin. Additionally provided is at least one coil 16 on the electrode. This coil 16 can broadcast at a fairly high frequency. As desired for a given application, the broadcasting electrode may be configured to be time multiplexed with the other broadcasting electrodes or configured to operate at a given frequency for a given electrode.

Figure 2:
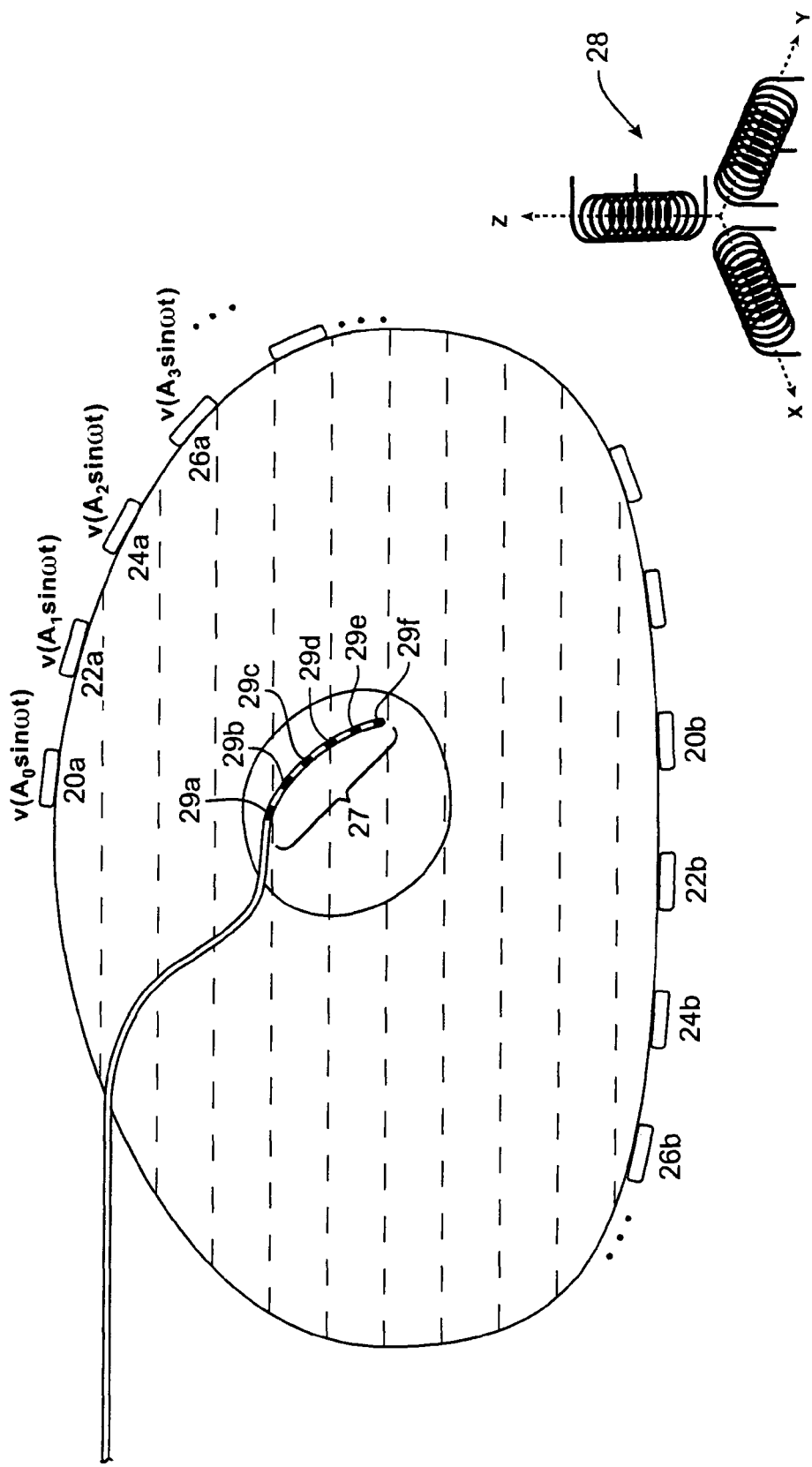
FIG. 2 provides a view of multiple pairs of circumferentially positioned electrodes as may be employed according to embodiments of the invention.

As summarized above, sets of two or more pairs of external electrodes as shown in FIG. 1 are employed in embodiments of the invention to generate the flat electric fields across the region of interest of the body. FIG. 2 illustrates a set of external broadcast electrode pairs arranged circumferentially about a torso of a subject in a manner sufficient to generate multiple substantially flat or linear electric field gradients across the torso and heart, which includes the target tissue location. As shown in FIG. 2, a set of several pairs, i.e., 20a and 20b, 22a and 22b, 24a and 24b, 26a and 26b, etc., of broadcasting electrodes are aligned in relation to each other at external locations on the torso of the subject. Following positioning on the surface of the body, each set of external electrode pairs are located in three dimensional space, e.g., by an external locating system 28 as shown in FIG. 2, in order to determine how to activate the broadcasting electrodes in a manner sufficient to produce the desired flat electric field(s). As such, the pairs of electrodes of the set of external electrodes are located on the body in absolute three dimensional space using the locating system 28. The electrodes use a broadcasting coil on each skin electrode and a locator, e.g., represented by the receive coils on the array of orthogonal coils 28 shown in FIG. 2. Each of these skin electrodes is then located by the computer in absolute three dimensional space. As the patient breaths and their chest wall goes up and down, those movements as determined by the skin electrodes are recorded by the computer. The locator 28 can be provided in a permanent location, such at the patient's bedside on a table, or otherwise near the patient, as desired.

Upon locating of the pairs of external broadcasting electrodes, these electrode locations are then employed to determine how they should be actuated in order to produce one or more substantially linear electrical field gradients across the torso and heart. This step may include entering the locations into a processor, e.g., present in a computer, and using the process to calculate the locations of the broadcast electrodes in three dimensional space. The processor can also be employed to command a certain voltage at each of the electrodes by sending a signal, such as a digital signal, nearly simultaneously to all the electrodes. The broadcast electrodes are operated in a manner that produces substantially flat electric fields across the torso. A first substantially flat electric field across the torso is illustrated in FIG. 2 by the series of parallel dashed lines. Each of the broadcast electrodes contributes in part to the generation of the field to produce the desired flat gradient. The flat gradient represented in FIG. 2 is distinguished from hyperbolic gradients which are produced using only a single pair of broadcast electrodes.

In the system shown in FIG. 2 as a cross section of the torso, centrally provided is a diagrammatically rendered heart in which an array 27 of sensing elements in the form of receive electrodes 29a to 29f are embedded. Shown on the skin situated around the cross section of the heart is an array of electrodes circumferentially positioned relative to the heart. Each electrode can be situated a set space apart, by example by about an inch. Other potential spacings for the broadcasting electrodes are from about 1 mm to about 200 mm, such as from about 5 mm to 50 mm, and in certain embodiments from about 10 to about 30 mm, e.g., about 20 mm.

Also shown in FIG. 2 is an example of one of the frequencies that is broadcast by the skin electrodes, where the electrodes broadcast at the frequency in a manner sufficient to generate the substantially linear or flat gradient electric field that is represented by the dashed lines. In this example, the highest amplitude at frequency $\omega$ is at the uppermost skin electrode, electrode 20a, and the lowest amplitude or a neutral amplitude is located at the bottom most electrode, or electrode 20b. All of the intermediate electrodes, such as electrodes 22a, 24a and 26a, have a lower amplitude than electrode 20a for frequency $\omega$. Electrode 24a has a lower amplitude than electrode 22a. Electrode 26a has a lower amplitude than electrode 24a, and so forth. In certain embodiments, the amplitudes range from about +10V to about –10V, such as from about +2V to about –2V and including from about +1V to –1V.

The amplitude of each of these skin electrodes is captured by the locator/computer in such a way that there is a substantially linear gradient in amplitude in real space between electrode 20a and electrode 20b at the bottom, as shown by the dashed lines. Even as the patient's chest goes up and down with breathing or other movements, one of these electrodes serves as a benchmark in three dimensional space. This benchmark can be selected as the electrode at the center of the heart or elsewhere, as it is an arbitrary point.

At the benchmark point, the amplitude does not change. The slope at that point also does not change. Even though the patient is breathing up and down, a gradient of AC potential is present through the cross section that stays constant. That is, one frequency where all the electrodes participate in creating a flat, tilted plane of potential through the body, i.e., a substantially linear gradient, is produced.

In some embodiments of the present invention, multiple frequencies may be broadcast simultaneously. The receiving electrodes 29a to 29f are each at a different carrier frequency. In addition to having electrode 20a to be at the highest amplitude of frequency 1, electrode 22a is at the highest amplitude of frequency 2. Electrode 22b is at the lowest amplitude for frequency 2 and electrode 24b is at the lowest amplitude for frequency 3. Electrode 24a is at the highest amplitude for frequency 3. These relative amplitudes are exemplary only, and the ordinary skilled artisan will readily recognize other useful variations. As illustrated in the figures, embodiments of the invention are characterized by having each electrode operate (i.e., broadcast) at a multiple frequencies at the same time, thereby contributing in part to each different substantially linear or flat gradient. As such, a given electrode of the set may be operating at two or more, such as three or more, 5 or more, 10 or more, etc., frequencies at the same time during generation of the electric field(s).

In this way, many different sloping planes of potential are produced, where each plane is distinguishable as part of a different substantially linear field gradient. Each of these planes may be produced at different frequency for as many sets of external electrode pairs as are provided. For example, if twenty electrodes are placed throughout the body, ten different planes may be produced from ten different electrode pairs. A lower or higher number of electrodes can also be provided. A higher density of electrodes is usefully employed when it is advantageous to produce a flatter set of planes, and to produce more directions in frequencies. In certain embodiments, a set is made up of non-sharing pairs of electrodes, such that each pair of electrodes is made up of its own electrodes. In yet other embodiments, two or more pair members of a set may share a common electrode, e.g., where two pairs are made by three electrodes etc.

Figure 3:
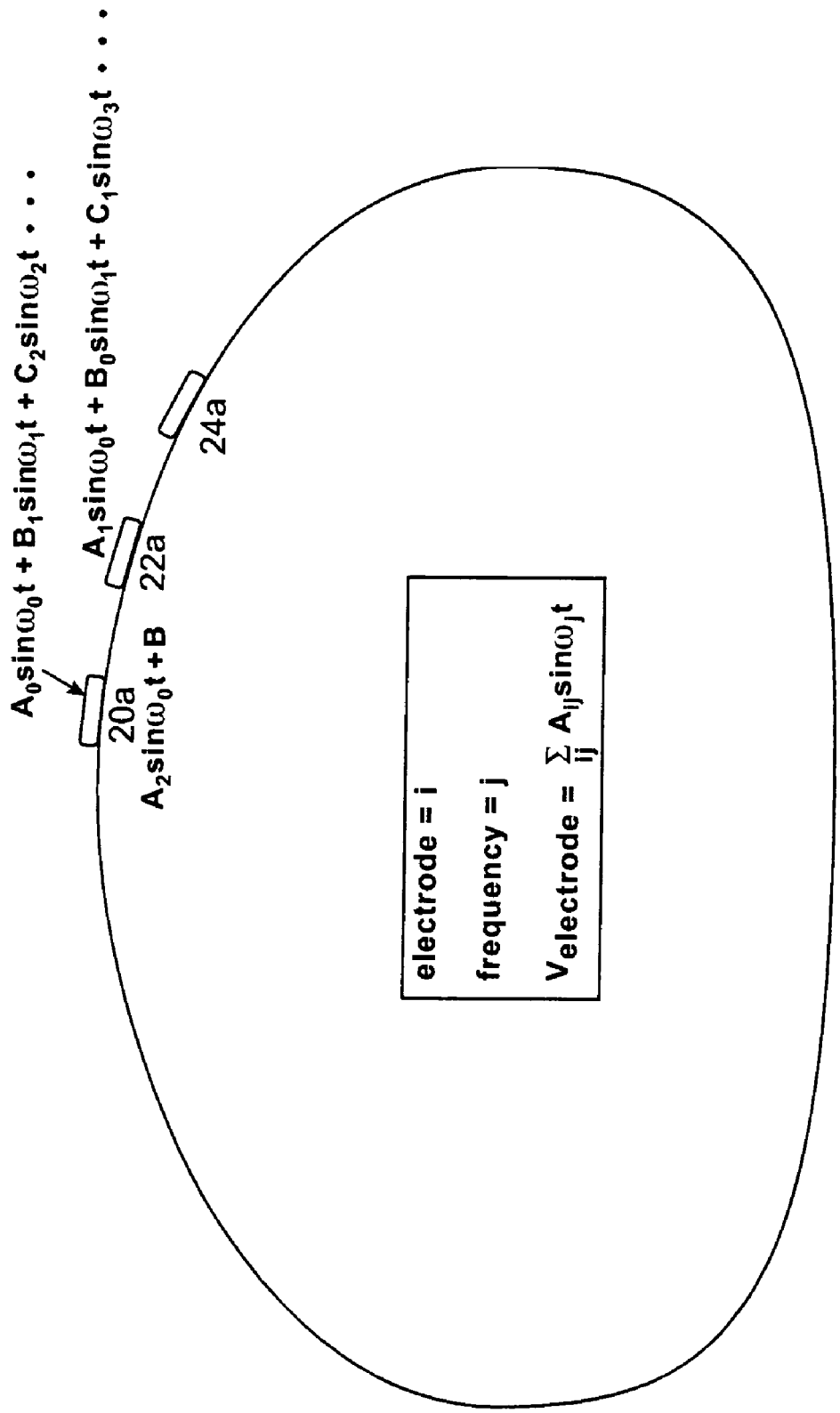
FIG. 3 provides an abbreviated calculation approach for the voltage determination at each electrode.

FIG. 3 provides examples of one approach to the mathematics of the voltage at each electrode. Each electrode broadcasts a voltage which corresponds to the summation of all of the voltages that are required to generate the desired linear field(s). By example, electrode 20a has an amplitude of $(A_0 \sin \omega_0 t)+(B_1 \sin \omega_1 t)+(C_2 \sin \omega_2 t)$, where in this case $A_0$ would be the largest amplitude for frequency $\omega_0$. $B_1$ would not be the largest amplitude for frequency $\omega_1$. $B_0 \omega_1$, the largest amplitude, is for electrode 22a. The largest amplitude for frequency 3 occurs at electrode 24a. Another way of describing this operation is that the voltage broadcast at each electrode is the summation for that electrode at a given frequency $A_{ij} \sin \omega_j t$, where the electrode is i and the frequency is j. In other words, the amplitude at electrode i is the sum of a variety of these amplitudes. The computer automatically calculates which coefficients create the flattest plane across the region of interest for each frequency. Each frequency has a different orientation of its plane.

Figure 4:
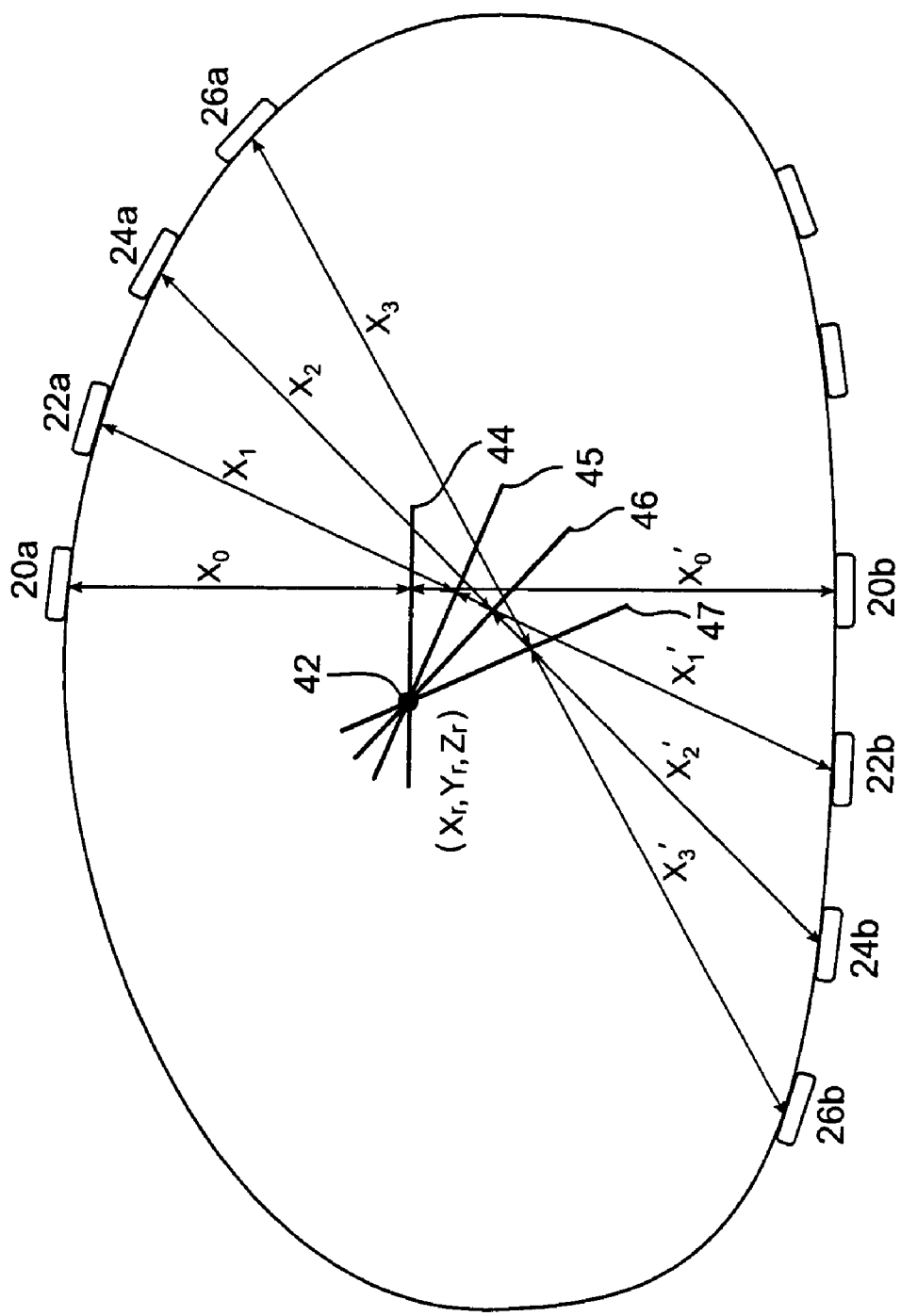
FIG. 4 provides a cross sectional view of the electrode array.

FIG. 4 provides the same cross section as shown in FIG. 2 and FIG. 3. Visible in FIG. 4 is a set of electrode pairs arranged circumferentially around the subject, e.g., in the form of an array of external broadcast electrodes, starting with 20a, 22a, 24a, and 26a, at the top and also at the bottom from 20b, 22b, 24b, 26b. Essentially, there are two distances between electrodes 20a and 20b, where these distances are denoted as $X_0$ and $X_0'$. These distances are between the receive electrode 42 and the associated broadcast electrode 20a or broadcast electrode 20b. At a different frequency, such as frequency 1, a different pair of distances is measured, $X_1$ and $X_1'$. These are the distances between the receive electrode 42 and broadcast electrode 22a and electrode 22b. A distance $X_2$ and $X_2'$ is measured between electrode broadcast electrode 24a and the receive electrode 42, and the receive electrode 42 and broadcast electrode 24b. These calculated distances are not actual, physical distances between the different electrodes. As shown here, these distances are perpendicular distances. The perpendicular distance is the distance along the axis between two opposed electrodes, i.e. a pair of the set of external electrodes, where the receive electrode 42 lies at a line perpendicular to that axis.

FIG. 4 is accurate in that between the pair 20a and 20b, there is a line 44 that is perpendicular to that line between 20a and 20b that intersects the receive electrode 42. This represents an iso-potential line 44 of the frequency broadcast at electrode 20a relative to electrode 20b at frequency 0. Iso-potential line 45 at frequency 1 is perpendicular to the axis of the line between electrode 22a and electrode 22b. Iso-potential line 46 at frequency 2 is perpendicular to the axis between electrode 24a and electrode 24b. Iso-potential line 47 at frequency 3 is perpendicular to the axis between electrode 26a and electrode 26b.

From these different distances, the locations of the electrodes 20a, 22a, 24a, 26a, 20b, 22b, 24b, and 26b are determined in either two or three dimensions. The computer or other control element has commanded what the electrical gradient is at the boundary conditions of the body. This approach produces relatively flat, straight iso-potential lines inside the body. These iso-potential lines are not perfectly straight, but are sufficiently straight to provide useful information, i.e., they are substantially linear. Therefore, the "distances" determined by the above described inventive embodiment are approximations of distances rather than exact distances.

The culmination of the above process results in the determination of a number of multiple distance measurements to the same point, but at different angles. Geometrical calculations establish where the electrode must be located in order to fit in all of these multiple equations simultaneously. In the case of two N electrodes, N equations of distance and unknowns are determined. By evaluating the linear field gradient dependent reading from a sensing element (receive electrode), the precise coordinates of the receive electrode are then calculated. These coordinates are used to determine the location of the sensing element (receive electrode). This process is accomplished for each receive electrode as desired. This treatment is individual because each receive electrode has a different set of $X_0$, $X_0'$, $X_1$, $X_1'$, $X_2$, $X_2'$, etc.

Each of these multiple explanations of distance improves the inventive approximation of the coordinates of the receive electrode. The more of these frequencies and orientations that are employed, the better the final approximation is for the location of the receive electrodes. Providing finer evaluation is a traditional approach in prior art tomography methods. Thus, using finer electrode positioning as above provides an electrical corollary to the prior art topographic method.

In addition to the method described above to determine the location of the sensing element, the methods of the present invention could also be used to determine the velocity or acceleration of the sensing element, using information from the same linear field gradient dependent readings.

Electromagnetic signals are also exploited by the present invention, where magnetic coils are utilized to locate the electrodes. The electromagnetic coils can also be used to broadcast at the receive electrode. However, it is simpler if electrical fields are used as contrasted to magnetic coil fields.

Figure 5:
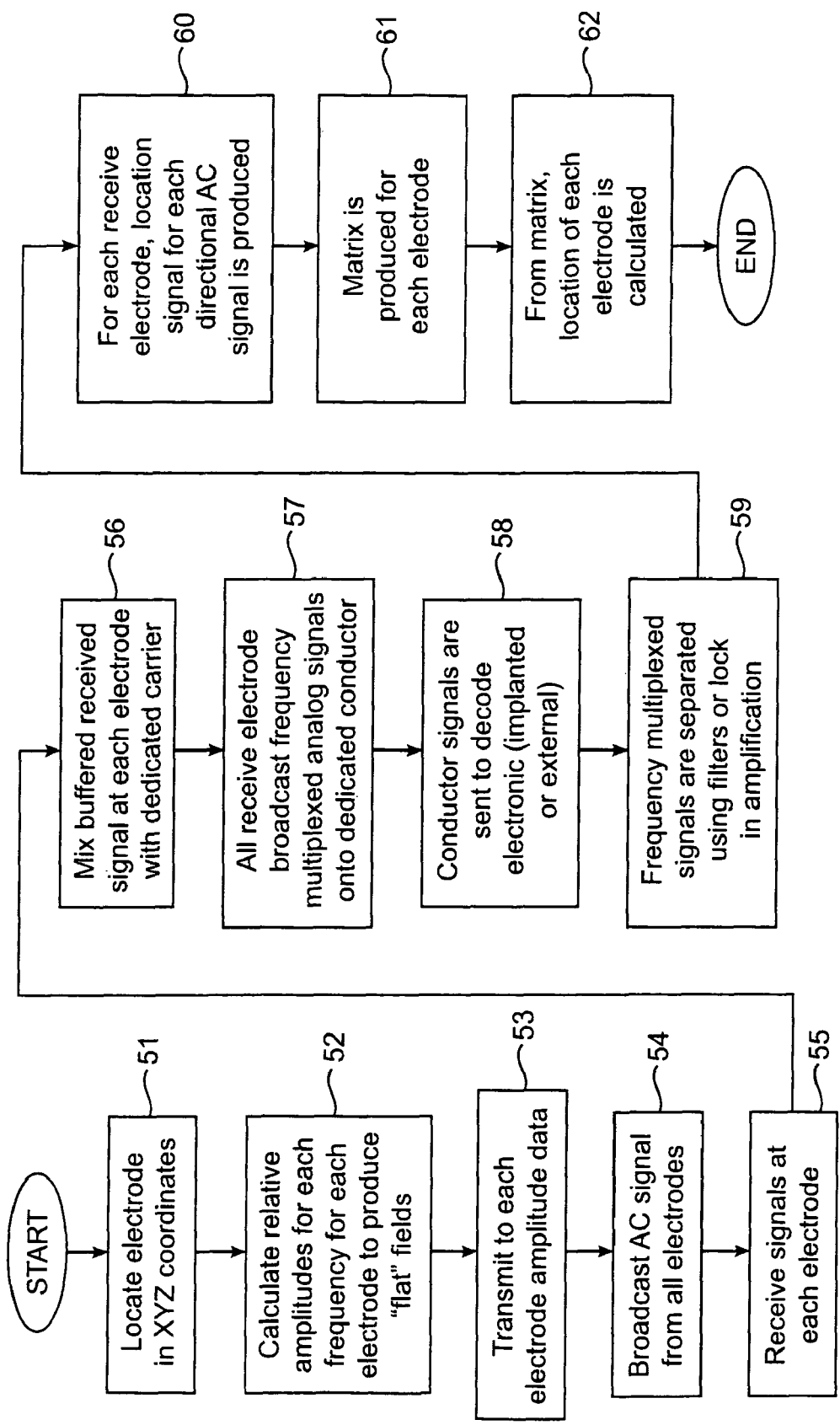
FIG. 5 is a flow diagram of the algorithm used to provide the necessary data calculations.

FIG. 5 provides a flow diagram which describes elements of an example of an embodiment of the inventive calculation process. FIG. 5 outlines an algorithm which can be used by a computer to perform some of the operations described above. Starting in the left hand corner labeled 51, the computer locates each external broadcast electrode in three dimensions, e.g., by using a locator device 28 as shown in FIG. 2. Each external broadcast electrode is assigned an instantaneous X Y Z coordinate. From its coil, each broadcast electrode broadcasts a signal that is picked up by the locator 28, e.g., depicted as an illustrative benchmark three pairs of coils in three different orientations. This step provides the necessary location data. In the embodiment shown in FIG. 2 with the locator device 28, a coil is located using three pairs of orthogonal coils, e.g., by using gradiometry or other convenient techniques, From those locations, the computer calculates relative amplitudes for each frequency and for each pair of electrodes. Each pair of electrodes is assigned a frequency where they are the maximum and minimum for that frequency. All of the other electrodes have intermediate amplitudes for that frequency. As a result, each electrode broadcasts a combination of all the frequencies for all the frequency pairs for all the electrode pairs. The computer also calculates (illustrated as box 52) what amplitude at each frequency would produce the flattest field, or the straightest iso-potential lines through the body, i.e., a substantially linear gradient. This calculation is based on the location of the electrodes.

The inventive method can be accomplished without knowledge of the intervening tissue inside the body. Alternately, knowledge of the intervening tissues can be exploited to improve the linearity inside the tissue. Information on intervening tissue can be obtained using any convenient protocol, e.g., by X-rays or MRI identification of the tissue type and size, by generally applicable assumptions as to anatomy, as well as by other methods. In the case where intervening tissues are characterized, it is not necessary to drive a purely linear relationship at the boundary condition. This approach can be modified somewhat either in phase, amplitude or frequency, to produce the flattest electrical fields in the region of interest. In the example here, the region of interest is the heart. However, the inventive method can be used to monitor other organs or regions, e.g., liver, stomach, lungs, etc., e.g., which may be of clinical importance.

At step 53, the amplitude, data and frequency data is transmitted to each broadcast electrode. The electrodes essentially have the frequency list. That list is typically preloaded into each electrode. Additionally, the electrodes can be provided instantaneous updates on amplitudes of those different frequencies. Based on this information, the electrodes are provided a modified broadcasting routine to broadcast the new set of amplitude per frequency data. The summation of frequencies, phase and amplitude information are calculated in each electrode. This summation is then broadcast at step 53 as a complex multi-frequency signal, e.g., in the form of an AC signal.

At step 54, the broadcast electrodes then broadcast their respect multi-frequency signal for which they have received instructions at step 53. The signal that is broadcast at each different broadcast electrode is different.

At step 55, each receive electrode receives this multiple frequency signal. By example, there can be a set (e.g., in the form of an array) of eight receive electrodes on a lead. The amplitudes of each of the signals are different at each of the receive electrodes. This is because the electrodes are located at a different place within the body. The gradients are different at each location as well. These receive signals can be in the form of amplitude at a given frequency.

In an alternative embodiment, using some of the inventors' quaternary electrode systems, e.g., as described in PCT application Ser. No. PCT/US2005/031559 published as WO 2006/029090 and PCT application Ser. No. PCT/US2005/046811 published as WO 2006/069322, the gradient at each frequency can be measured as well. As such, the reading obtained from the receive electrode will include a gradient measure or value, where this gradient reading can then be employed locate the position of the receive electrode, and thereby the tissue location of interest, e.g., to monitor movement of the tissue of the location of interest. This approach can provide even higher levels of resolutions of location.

At step 56, the signals are mixed with a carrier signal for each receive electrode. The signals may include either the amplitude alone or the amplitude and gradient signals together. Each receive electrode is assigned a different carrier frequency. This complex multi-frequency analog signal is then mixed in with another higher level frequency system. Frequency multiplexing is achieved by broadcasting the signal down the carrier. In other embodiments of the system, other techniques are employed, and can be selected for their particular advantages in certain applications. In one such embodiment the receive signals are digitized and perform all the signal processing of decoding of the signals in terms of its relative location. The data sent back is provided in terms of numbers instead of analog format.

FIG. 5 provides a process flow of one embodiment of the present invention. Shown is the method which keeps the signals in the analog domain until the signals are either outside the body or in the can. Further signal processing occurs elsewhere, e.g., in an implanted processor (such as may be present in an implantable pulse generator or "can," or at an external location. This feature is provided as a matter of convenience to keep the power consumption of the electronics and the lead at a minimum, among other advantages.

In an alternate embodiment, processing capability is provided, e.g., built into, the chips at each receive electrode. When implanted in the heart, additional functionality is provided. An appropriate, optimized choice of location for the decode electronics for a particular application, e.g., at the site of the receive electrode, in a "can," or external, may be readily determined based on a given application. The flow chart of FIG. 5 is optimized for as much electronics outside the body as possible, and the minimum electronics on the implant as possible.

Referring now to step 57 on the flow chart of FIG. 5, all the receive electrodes are decoded, e.g., by broadcasting a frequency multiplex analog signal onto a dedicated conductor. There is one conductor receiving eight different frequency channels for eight different receive electrodes. Each of those frequencies mixes multiple frequencies as well from the originally broadcast signals.

Referring now to step 58 on the flow chart of FIG. 5, the conductor signals are sent to the decode electronics, e.g., positioned at an internal or external location. These decode electronics may be either implanted or external. If the decode electronics are external, a communications link such as an RF link to external electronics, where the signal is then broadcast, may be employed. At the decode electronics step 59, frequency multiplexing signals are separated using any convenient approach, e.g., by using filters or lock-in amplification. While not shown here, time multiplexing can also be employed. In the embodiment depicted in FIG. 5, the eight frequency multiplexing signals are separated into signals using filters or lock-in amplifiers. These signals represent those signals received at each of the eight receive electrodes.

Referring now to step 60 in FIG. 5, each electrode location signal is compared with a lock-in amplifier for each of the original frequencies broadcast between pairs of electrodes. Where twenty electrodes are placed around the body, ten electrode pairs are available with ten broadcast frequencies. Ten lock-in amplifiers are also provided, one for each of those ten frequencies. The output of those lock-in amplifiers are the values $X_1$ and $X_1'$, or each frequency produces a pair of dimensional numbers X and X'.

The configuration in this inventive embodiment allows creation of a matrix for each electrode, a depicted at step 61. The matrix provides an array of equations, where for each pair of electrodes there is a dimension, $X_0$ and $X_0'$ for example.

Orientation and location estimate of that distance is provided using the locations of the electrodes. Multiple electrodes and multiple frequency orientations are available at each of those frequencies.

From this matrix, a best estimate of the location in XYZ coordinates of each of the eight receive electrodes is produced at step 62. This can be accomplished using any convenient approach, such as by using a least squared algorithm, or inversion of matrix algorithm, among other approaches.

Where desired, the operation of the external electrodes can be manipulated in a manner sufficient to produce electrical fields that generate zero values in certain of the fields of the matrix, thereby reducing the processing requirements that are employed to determine the locations of the receive electrodes. Such embodiments may be desirable where, for example, more limited processing capacity is available, e.g., where the processing is happening at an internal location, e.g., in a can or even at the site of the receive electrode, e.g., as described above. For example, the gradients can be manipulated or "spun" such that their orientation is normal to the motion of interest of the receive electrode, which can serve to "zero" certain values of the matrix and thereby simplify the processing calculations required to obtain the desired location data.

Once the locations of each of the eight receive electrodes are determined, this data provides the basis for evaluation of a number of different useful cardiac performance parameters, e.g., how synchronized the motion of these receive electrodes are relative to each other. Also, the synchrony relative to other electrodes that are located within the torso can also be determined.

For example, one can have one receive electrode located in the right atrium and one receive electrode located in the right ventricle. Eight receive electrodes can also be located over the left ventricular wall. The relative location of each of these eight electrodes in the left ventricular wall is measured relative to the right ventricle receive electrode. Based on this data, a measure of dyssynchrony is determined, which is employed to optimize cardiac resynchronization therapy.

Similarly from the example immediately above, the location parameters may be used to measure the absolute volume of the ventricle. The changes in ventricular volume are dynamically evaluated over time. From this data, the stroke volume and ejection fraction of the heart can be estimated, along with other parameters of interest to a clinician.

While there are multiple ways of decoding the signal, an element of certain embodiments of the present invention is the concept of broadcasting at different, multiple frequencies oriented differently around the circumference of a patient's torso. In the simpler embodiments described above, a two dimensional array of electrodes positioned on a belt around the torso is described.

A more complex embodiment of the present invention requires at least two external electrode belts, separated on the torso at some distance. With this device configuration, the broadcast electrodes are located in three dimensions, X, Y and Z, where Z is essentially along the long axis of the body, between the two belts. The mathematics used to evaluate the data from this system are similar to that described above for simpler embodiments. However, the calculations address three dimensional space instead of two dimensional space.

In both two and three dimensional space embodiments, multiple substantially "flat" or linear fields are provided, with AC fields at different frequencies and different orientations. Whether the fields are designed to be orientated in a two dimensional system or a three dimensional system is up to the designer when weighting the advantages and disadvantages of each system as paired with a clinical application. Similarly, the designer choice of whether the receive electrodes deconvolve the information at the electrode or simply transmit the information to a centrally located deconvolver is selected based on the needs of the system.

Systems

Aspects of the invention include systems, including implantable medical devices and systems, which include the devices of the invention and can be employed to practice methods according to the invention e.g., as described above. The systems may also be configured to perform a number of different functions, including but not limited to electrical stimulation applications, e.g., for medical purposes, such as pacing, CRT, etc.

The systems may have a number of different components or elements. Elements that are present in the systems may include a sensing element such as implantable receive electrodes, a set of external broadcast electrodes or any external substantially linear field gradient generator, a locator for locating external broadcast electrodes or source of substantially linear field gradient in three dimensional space, a signal processing element configured to employ a reading obtained from the sensing element, and programming for practicing the methods, e.g., for implementing the protocol depicted in FIG. 5, where the programming may be implemented in an implanted or external processor, e.g., as described above.

In certain embodiments of the subject systems, one or more receive electrodes of the invention are electrically coupled to at least one elongated conductive member, e.g., an elongated conductive member present in a lead, such as a cardiovascular or vascular lead. In certain embodiments, the elongated conductive member is part of a multiplex lead, e.g., as described in Published PCT Application No. WO 2004/052182 and U.S. patent application Ser. No. 10/734,490, the disclosure of which is herein incorporated by reference. In some embodiments of the invention, the devices and systems may include onboard logic circuitry or a processor, e.g., present in a central control unit, such as a pacemaker can. In these embodiments, the central control unit may be electrically coupled to one or more receive electrodes via one or more conductive members.

In certain embodiments of the subject systems, one or more sets of electrodes are electrically coupled to at least one elongated conductive member, e.g., an elongated conductive member present in a lead, such as a cardiovascular or vascular lead. In certain embodiments, the elongated conductive member is part of a multiplex lead. Multiplex lead structures may include 2 or more satellites, such as 3 or more, 4 or more, 5 or more, 10 or more, 15 or more, 20 or more, etc. as desired, where in certain embodiments multiplex leads have a fewer number of conductive members than satellites. In certain embodiments, the multiplex leads include 3 or less wires, such as only 2 wires or only 1 wire. Multiplex lead structures of interest include those described in application Ser. Nos. 10/734,490 titled "Method and System for Monitoring and Treating Hemodynamic Parameters" filed on Dec. 11, 2003; PCT/US2005/031559 titled "Methods and Apparatus for Tissue Activation and Monitoring," filed on Sep. 1, 2006; PCT/US2005/46811 titled "Implantable Addressable Segmented Electrodes" filed on Dec. 22, 2005; PCT/US2005/46815 titled "Implantable Hermetically Sealed Structures" filed on Dec. 22, 2005; 60/793,295 titled "High Phrenic, Low Pacing Capture Threshold Implantable Addressable Segmented Electrodes" filed on Apr. 18, 2006 and 60/807,289 titled "High Phrenic, Low Capture Threshold Pacing Devices and Methods," filed Jul. 13, 2006; the disclosures of the various multiplex lead structures of these applications being herein incorporated by reference. In some embodiments of the invention, the devices and systems may include onboard logic circuitry or a processor, e.g., present in a central control unit, such as a pacemaker can. In these embodiments, the central control unit may be electrically coupled to the lead by a connector, such as a proximal end IS-1 connection.

In certain embodiments, the receive electrodes are segmented electrode structures. By segmented electrode structure is meant an electrode structure that includes two or more, e.g., three or more, including four or more, disparate electrode elements. Embodiments of segmented electrode structures are disclosed in application Ser. Nos. PCT/US2005/031559 titled "Methods and Apparatus for Tissue Activation and Monitoring," filed on Sep. 1, 2006; PCT/US2005/46811 titled "Implantable Addressable Segmented Electrodes" filed on Dec. 22, 2005; PCT/US2005/46815 titled "Implantable Hermetically Sealed Structures" filed on Dec. 22, 2005; 60/1793,295 titled "High Phrenic, Low Pacing Capture Threshold Implantable Addressable Segmented Electrodes" filed on Apr. 18, 2006 and 60/807,289 titled "High Phrenic, Low Capture Threshold Pacing Devices and Methods," filed Jul. 13, 2006; the disclosures of the various segmented electrode structures of these applications being herein incorporated by reference.

In certain embodiments, the receive electrodes are "addressable" electrode structures. Addressable electrode structures include structures having one or more electrode elements directly coupled to control circuitry, e.g., present on an integrated circuit (IC). Addressable electrode structures include satellite structures that include one more electrode elements directly coupled to an IC and configured to be placed along a lead. Examples of addressable electrode structures that include an IC are disclosed in application Ser. Nos. 10/734,490 titled "Method and System for Monitoring and Treating Hemodynamic Parameters" filed on Dec. 11, 2003; PCT/US2005/031559 titled "Methods and Apparatus for Tissue Activation and Monitoring," filed on Sep. 1, 2006; PCT/US2005/46811 titled "Implantable Addressable Segmented Electrodes" filed on Dec. 22, 2005; PCT/US2005/46815 titled "Implantable Hermetically Sealed Structures" filed on Dec. 22, 2005; 60/793,295 titled "High Phrenic, Low Pacing Capture Threshold Implantable Addressable Segmented Electrodes" filed on Apr. 18, 2006 and 60/807,289 titled "High Phrenic, Low Capture Threshold Pacing Devices and Methods," filed Jul. 13, 2006; the disclosures of the various addressable electrode structures of these applications being herein incorporated by reference.

Embodiments of the subjects systems may incorporate one or more effector elements. The effectors may be intended for collecting data, such as but not limited to pressure data, volume data, dimension data, temperature data, oxygen or carbon dioxide concentration data, hematocrit data, electrical conductivity data, electrical potential data, pH data, chemical data, blood flow rate data, thermal conductivity data, optical property data, cross-sectional area data, viscosity data, radiation data and the like. As such, the effectors may be sensors, e.g., temperature sensors, accelerometers, ultrasound transmitters or receivers, AC voltage sensors, potential sensors, current sensors, etc. Alternatively, the effectors may be intended for actuation or intervention, such as providing an electrical current or voltage, setting an electrical potential, heating a substance or area, inducing a pressure change, releasing or capturing a material or substance, emitting light, emitting sonic or ultrasound energy, emitting radiation and the like.

Effectors of interest include, but are not limited to, those effectors described in the following applications by at least some of the inventors of the present application; U.S. patent application Ser. No. 10/734,490 published as 20040193021 titled: "Method And System For Monitoring And Treating Hemodynamic Parameters"; U.S. patent application Ser. No. 11/219,305 published as 20060058588 titled: "Methods And Apparatus For Tissue Activation And Monitoring"; International Application No. PCT/US2005/046815 titled: "Implantable Addressable Segmented Electrodes"; U.S. patent application Ser. No. 11/324,196 titled "Implantable Accelerometer-Based Cardiac Wall Position Detector"; U.S. patent application Ser. No. 10/764,429, entitled "Method and Apparatus for Enhancing Cardiac Pacing," U.S. patent application Ser. No. 10/764,127, entitled "Methods and Systems for Measuring Cardiac Parameters," U.S. patent application Ser. No. 10/764,125, entitled "Method and System for Remote Hemodynamic Monitoring", International Application No. PCT/US2005/046815 titled: "Implantable Hermetically Sealed Structures"; U.S. application Ser. No. 11/368,259 titled: "Fiberoptic Tissue Motion Sensor", International Application No. PCT/US2004/041430 titled: "Implantable Pressure Sensors"; U.S. patent application Ser. No. 11/249,152 entitled "Implantable Doppler Tomography System," and claiming priority to: U.S. Provisional Patent Application No. 60/617,618; International Application Serial No. PCT/USUS05/39535 titled "Cardiac Motion Characterization by Strain Gauge". These applications are incorporated in their entirety by reference herein.

Use of the systems may include visualization of data obtained with the devices. Some of the present inventors have developed a variety of display and software tools to coordinate multiple sources of sensor information which will be gathered by use of the inventive systems. Examples of these can be seen in international PCT application Ser. No. PCT/US2006/012246; the disclosure of which application, as well as the priority applications thereof are incorporated in their entirety by reference herein.

Data obtained in accordance with the invention, as desired, can be recorded by an implantable computer. Such data can be periodically uploaded to computer systems and computer networks, including the Internet, for automated or manual analysis.

Uplink and downlink telemetry capabilities may be provided in a given implantable system to enable communication with either a remotely located external medical device or a more proximal medical device on the patient's body or another multi-chamber monitor/therapy delivery system in the patient's body. The stored physiologic data of the types described above as well as real-time generated physiologic data and non-physiologic data can be transmitted by uplink RF telemetry from the system to the external programmer or other remote medical device in response to a downlink telemetry transmitted interrogation command. The real-time physiologic data typically includes real time sampled signal levels, e.g., intracardiac electrocardiogram amplitude values, and sensor output signals including dimension signals developed in accordance with the invention. The non-physiologic patient data includes currently programmed device operating modes and parameter values, battery condition, device ID, patient ID, implantation dates, device programming history, real time event markers, and the like. In the context of implantable pacemakers and ICDs, such patient data includes programmed sense amplifier sensitivity, pacing or cardioversion pulse amplitude, energy, and pulse width, pacing or cardioversion lead impedance, and accumulated statistics related to device performance, e.g., data related to detected arrhythmia episodes and applied therapies. The multi-chamber monitor/therapy delivery system thus develops a variety of such real-time or stored, physiologic or non-physiologic, data, and such developed data is collectively referred to herein as "patient data".

Utility

The external continuous field tomography methods of evaluating tissue location movement find use in a variety of different applications. As indicated above, one application of the subject invention is for use in cardiac resynchronization therapy (CRT)(i.e., biventricular pacing). CRT remedies the delayed left ventricular mechanics of heart failure patients. In a desynchronized heart, the interventricular septum will often contract ahead of portions of the free wall of the left ventricle. In such a situation, where the time course of ventricular contraction is prolonged, the aggregate amount of work performed by the left ventricle against the intraventricular pressure is substantial. However, the actual work delivered on the body in the form of stroke volume and effective cardiac output is lower than would otherwise be expected. Using the subject continuous field tomography approach, the electromechanical delay of the left lateral ventricle can be evaluated and the resultant data employed in CRT, e.g., using the approaches reviewed above and/or known in the art and reviewed at Col. 22, lines 5 to Col. 24, line 34 ff of U.S. Pat. No. 6,795,732, the disclosure of which is herein incorporated by reference.

In a fully implantable system the location of the pacing electrodes on multi electrode leads and pacing timing parameters are continuously optimized by the pacemaker. The subject methods and devices can be used to determine the cardiac wall motion and timing of cardiac wall motion of a first cardiac wall (e.g. the interventricular septum) relative to a second cardiac wall (e.g. the free wall of the left ventricle) to detect ventricular mechanical dyssynchrony. The pacemaker can then determine the location and parameters which minimize intraventricular dyssynchrony, interventricular dyssynchrony, or electromechanical delay of the left ventricle lateral wall in order to optimize CRT. This cardiac wall motion sensing system can also be used during the placement procedure of the cardiac leads in order to optimize CRT. An external controller could be connected to the cardiac leads and a skin patch electrode during placement of the leads. The skin patch acts as the reference electrode until the pacemaker is connected to the leads. In this scenario, for example, the optimal left ventricle cardiac vein location for CRT is determined by acutely measuring intraventricular dyssynchrony.

The subject methods and devices can be used to adjust a resynchronization pacemaker either acutely in an open loop fashion or on a nearly continuous basis in a closed loop fashion.

Other uses for this system are as an ischemia detector. It is well understood that in the event of acute ischemic events one of the first indications of such ischemia is akinesis, i.e., decreased wall motion of the ischemic tissue as the muscle becomes stiffened. A Wall motion system would be a very sensitive indicator of an ischemic process, by ratio metrically comparing the local wall motion to a global parameter such as pressure; this has been previously described in another Proteus patent. One can derive important information about unmonitored wall segments and their potential ischemia. For example, if an unmonitored section became ischemic, the monitored segment would have to work harder and have relatively greater motion in order to maintain systemic pressure and therefore ratio metric analysis would reveal that fact.

Another application of such position indicators that record wall motion is as a superior arrhythmia detection circuit. Current arrhythmia detection circuits rely on electrical activity within the heart. Such algorithms are therefore susceptible to confusing electrical noise for an arrhythmia. There is also the potential for misidentifying or mischaracterizing arrhythmia based on electrical events when mechanical analysis would reveal a different underlying physiologic process. Therefore the current invention could also be adapted to develop a superior arrhythmia detection and categorization algorithm.

Additional applications in which the subject invention finds use include, but are not limited to: the detection of electromechanical dissociation during pacing or arrhythmias, differentiation of hemodynamically significant and insignificant ventricular tachycardias, monitoring of cardiac output, mechanical confirmation of capture or loss of capture for autocapture algorithms, optimization of multi-site pacing for heart failure, rate responsive pacing based on myocardial contractility, detection of syncope, detection or classification of atrial and ventricular tachyarrhythmias, automatic adjustment of sense amplifier sensitivity based on detection of mechanical events, determination of pacemaker mode switching, determining the need for fast and aggressive versus slower and less aggressive antitachyarrhythmia therapies, or determining the need to compensate for a weakly beating heart after therapy delivery (where these representative applications are reviewed in greater detail in U.S. Pat. No. 6,795, 732, the disclosure of which is herein incorporated by reference), and the like.

In certain embodiments, the subject invention is employed to overcome barriers to advances in the pharmacologic management of CHF, which advances are slowed by the inability to physiologically stratify patients and individually evaluate response to variations in therapy. It is widely accepted that optimal medical therapy for CHF involves the simultaneous administration of several pharmacologic agents. Progress in adding new agents or adjusting the relative doses of existing agents is slowed by the need to rely solely on time-consuming and expensive long-term morbidity and mortality trials. In addition, the presumed homogeneity of clinical trial patient populations may often be erroneous since patients in similar symptomatic categories are often assumed to be physiologically similar. It is desirable to provide implantable systems designed to capture important cardiac performance and patient compliance data so that acute effects of medication regimen variation may be accurately quantified. This may lead to surrogate endpoints valuable in designing improved drug treatment regimens for eventual testing in longer-term randomized morbidity and mortality studies. In addition, quantitative hemodynamic analysis may permit better segregation of drug responders from non-responders thereby allowing therapies with promising effects to be detected, appropriately evaluated and eventually approved for marketing. The present invention allows for the above. In certain embodiments, the present invention is used in conjunction with the Pharma-informatics system, as described in PCT Application Ser. No. PCT/US2006/016370 filed on Apr. 28, 2006; the disclosure of which is herein incorporated by reference.

Non-cardiac applications will be readily apparent to the skilled artisan, such as, by example, measuring the congestion in the lungs, determining how much fluid is in the brain, assessing distention of the urinary bladder. Other applications also include assessing variable characteristics of many organs of the body such as the stomach. In that case, after someone has taken a meal, the present invention allows measurement of the stomach to determine that this has occurred. Because of the inherently numeric nature of the data from the present invention, these patients can be automatically stimulated to stop eating, in the case of overeating, or encouraged to eat, in the case of anorexia. The present inventive system can also be employed to measure the fluid fill of a patient's legs to assess edema, or other various clinical applications.

Computer Readable Medium

One or more aspects of the subject invention may be in the form of computer readable storage media having a processing program stored thereon for implementing the subject methods. The computer readable storage media may be, for example, a defined composition of matter, e.g., a solid or liquid which has a defined structure, e.g., in the form of a computer disk or CD, a floppy disc, a magnetic "hard card", a server, or any other computer readable media capable of containing data or the like, stored electronically, magnetically, optically or by other means. Accordingly, the processing program embodying steps for carrying-out the subject methods may be transferred or communicated to a processor, e.g., by using a computer network, server, or other interface connection, e.g., the Internet, or other relay means.

More specifically, a processor with a computer readable medium may include stored programming embodying an algorithm for carrying out the subject methods. Accordingly, such a stored algorithm is configured to, or is otherwise capable of, practicing the subject methods, e.g., by operating an implantable medical device to perform the subject methods. The subject algorithm and associated processor may also be capable of implementing the appropriate adjustment(s).

Of particular interest in certain embodiments are systems loaded with such computer readable storage mediums such that the systems are configured to practice the subject methods.

Kits

As summarized above, also provided are kits for use in practicing the subject methods. The kits at least include a computer readable storage medium, as described above. The computer readable medium may be a component of other devices or systems, or components thereof, in the kit, such as a processor, an adaptor module, a pacemaker, etc. The kits and systems may also include a number of optional components that find use with the subject energy sources, including but not limited to, implantation devices, etc.

In certain embodiments of the subject kits, the kits will further include instructions for using the subject devices or elements for obtaining the same (e.g., a website URL directing the user to a webpage which provides the instructions), where these instructions are typically printed on a substrate, which substrate may be one or more of: a package insert, the packaging, reagent containers and the like. In the subject kits, the one or more components are present in the same or different containers, as may be convenient or desirable.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

What is claimed is:

1. A method of evaluating a tissue location in a subject, the method comprising:
    (a) generating a substantially linear field gradient in the subject across the tissue location by broadcasting from a plurality of broadcasting electrodes coupled to a signal generator a respective number of multi-frequency signals, wherein each one of the multi-frequency signals is a summation of signals with different frequencies and wherein the signals with the different frequencies in the each one of the multi-frequency signals are assigned with corresponding amplitudes to form the substantially linear field gradient;
    (b) obtaining a linear field gradient dependent reading from a sensing element, wherein the sensing element is configured to physically attach to the tissue location with an attachment element such that movement of the sensing element coincides with movement of the tissue location and wherein the linear field gradient dependent reading is associated with a location of the sensing element in the substantially linear field gradient; and
    (c) evaluating the tissue location based on the linear field gradient dependent reading.

2. The method according to claim 1, wherein the substantially linear field gradient is a substantially linear electric field gradient.

3. The method according to claim 2, wherein the plurality of broadcasting electrodes is adapted to contact the subject externally.

4. The method according to claim 3, wherein each pair of the plurality of broadcasting electrodes comprises two electrodes.

5. The method according to claim 3, wherein at least two pairs of the plurality of broadcasting electrodes share a common electrode.

6. The method according to claim 3, wherein the plurality of broadcasting electrodes comprises three or more electrode pairs.

7. The method according to claim 3, wherein the plurality of broadcasting electrodes comprises electrode pairs arranged circumferentially around a portion of the subject.

8. The method according to claim 2, wherein the linear field gradient dependent reading comprises a voltage.

9. The method according to claim 8, wherein the voltage is an AC voltage.

10. The method according to claim 2, wherein the generating the substantially linear field gradient comprises generating two or more distinguishable substantially linear electric field gradients.

11. The method according to claim 10, wherein the two or more distinguishable substantially linear electric field gradients differ from each other by frequency.

12. The method according to claim 1, wherein the evaluating comprises determining location of the sensing element based on the linear field gradient dependent reading.

13. The method according to claim 1, wherein the evaluating comprises determining velocity of the sensing element based on the linear field gradient dependent reading.

14. The method according to claim 1, wherein the evaluating comprises determining acceleration of the sensing element based on the linear field gradient dependent reading.

15. The method according to claim 1, wherein the tissue location is a cardiac location.

16. The method according to claim 15, wherein the cardiac location is a heart wall location.

17. The method according to claim 1, wherein the sensing element is a receive electrode.

18. The method according to claim 17, wherein the receive electrode is present on a lead.

19. The method according to claim 1, wherein the obtaining the linear field gradient dependent reading is performed at least twice over a duration of time.

20. The method according to claim 1, wherein the evaluating the tissue location comprises determining timing of cardiac wall motion of the subject.

21. The method according to claim 1, wherein the evaluating the tissue location comprises determining cardiac wall motion of a first cardiac wall relative to a second cardiac wall.

22. The method according to claim 1, wherein the evaluating the tissue location comprises determining timing of cardiac wall motion of a first cardiac wall relative to a second cardiac wall.

23. The method according to claim 1, wherein the evaluating the tissue location comprises detecting ventricular mechanical dyssynchrony.

24. The method according to claim 23, wherein the evaluating the tissue location further comprises performing cardiac resynchronization therapy upon the detecting the ventricular mechanical dyssynchrony.

25. A system of evaluating a tissue location in a subject, the system comprising:
   (a) a plurality of broadcasting electrodes coupled to a signal generator and configured to generate a substantially linear field gradient in the subject across the tissue location by broadcasting a respective number of multi-frequency signals, wherein each one of the multi-frequency signals is a summation of signals with different frequencies and wherein the signals with the different frequencies in the each one of the multi-frequency signals are assigned with corresponding amplitudes to form the substantially linear field gradient;
   (b) a sensing element configured to obtain a linear field gradient dependent reading, wherein the sensing element is configured to physically attach to the tissue location with an attachment element such that movement of the sensing element coincides with movement of the tissue location and wherein the linear field gradient dependent reading is associated with a location of the sensing element in the substantially linear field gradient;
   (c) a signal processing element configured to evaluate the linear field gradient dependent reading to determine the tissue location.

* * * * *